(12) United States Patent
Alkhoury

(10) Patent No.: US 6,397,662 B1
(45) Date of Patent: Jun. 4, 2002

(54) GAS CONCENTRATION METER AND INSULATING GLASS ASSEMBLY AND METHOD THEREOF

(75) Inventor: Elie Alkhoury, Orangeville (CA)

(73) Assignee: CAN-BEST Building Sciences Corporation, Brampton (CA)

( * ) Notice: Subject to any disclaimer, the term of this patent is extended or adjusted under 35 U.S.C. 154(b) by 0 days.

(21) Appl. No.: 09/504,810

(22) Filed: Feb. 16, 2000

(51) Int. Cl.[7] .......................... G01N 7/00; G01M 3/04; G01L 7/00
(52) U.S. Cl. ...................... 73/31.04; 73/40; 73/700
(58) Field of Search ...................... 73/31.04, 31.05, 73/40, 700, 753, 170.25; 171/142

(56) References Cited

U.S. PATENT DOCUMENTS

| | | | |
|---|---|---|---|
| 1,336,211 A | | 4/1920 | Duffy |
| 2,125,372 A | | 8/1938 | Fox |
| 2,880,475 A | | 4/1959 | Mills |
| 3,126,439 A | * | 3/1964 | Denholm et al. ............. 174/31 |
| 3,763,691 A | * | 10/1973 | McMaster et al. ....... 73/170.25 |
| 4,835,341 A | * | 5/1989 | Katz et al. .................. 171/142 |
| 5,299,399 A | | 4/1994 | Baier et al. |
| 5,591,896 A | * | 1/1997 | Lin ........................... 73/31.05 |

* cited by examiner

Primary Examiner—Hezron Williams
Assistant Examiner—Jay L. Politzer
(74) Attorney, Agent, or Firm—Eugene J. A. Gierczak

(57) ABSTRACT

The system includes an access assembly for communicating with the gas filled insulating units, flexible electrodes for insertion through the access assembly to the gas and for sensing the concentration of the gas, and a meter for measuring and displaying the concentration of the gas that is sensed through the electrodes.

10 Claims, 7 Drawing Sheets

GAS CONCENTRATION METER AND INSULATING GLASS ASSEMBLY AND METHOD THEREOF

FIELD OF THE INVENTION

This invention relates in general to a system for measuring a gas sealed within an insulating glass assembly, and more particularly a gas concentration meter and method used for measuring the concentration of a gas within a sealed cavity or window assembly and a means of providing access to the sealed cavity.

BACKGROUND OF THE INVENTION

Due to the high cost of heating and cooling in most building structures, high efficiency and energy saving means are desirable for fenestration systems such as windows, doors, curtain walls, skylights or the like. Typically such systems include sealed insulating glass units filled with an inert gas. Traditionally these insulating systems have had an insulating air space or vacuum between the panels, which recently included a gas such as Argon to improve thermal performance. The inclusion of the gas is to provide additional insulation or resistance to thermal conductivity. Argon is the gas predominantly used due to its high benefit/cost ratio.

Over time the gas may escape or dissipate due to faulty seals of the like, which negates the beneficial effects of the insulating windows and results in increased energy costs. Due to the nature of the gases involved as described above, it is difficult to determine how much of the gas has escaped, and therefore what concentration of gas is left in the glass assembly. Furthermore if the gas concentration is found lower than the promised or the pre-selected level, the sealed insulating glass unit cannot generally be replenished without destroying the frame or seal of the fenestration system.

Several methods for measuring gas concentration in insulating glass units do exist today. However, such methods require sampling and analysis of the gas in the insulating glass unit's cavity. The use of such methods is severely limited, as the sampling of gas within the cavity cannot be performed on an insulating glass unit once it is glazed in place. Once the insulating unit is glazed in place, the edge seal becomes inaccessible. Any attempt to carry out sampling of the insulating glass unit is made at the risk of damaging the edge seal, which will promote insulating unit failure in a very short period of time.

Presently, buyers of gas-filled sealed units can only rely on the supplier's assuring words that the supplied units do contain insulating gas within the insulating cavity. As the fill gas is colorless and odorless, and inaccessible, there is no means of verifying such claims. Currently, insulating gas unit manufacturers may be certified that they comply with National Standards regarding gas concentration test requirements. Due to the lack of a more practical test method, the only reliable method that has been adopted by the Standard is gas chromatography. This method, however, requires sampling of gas in inaccessible cavity, and use of highly specialized analytical equipment and technicians to operate under strict laboratory conditions.

Current method of determining gas concentration involves measuring of Oxygen concentration in the cavity as it relates to presence of air. Other methods (under development) may be used to measure the concentration of a gas within the sealed units consist of applying a high voltage electrical current in the range of 10,000 to 20,000 volts across the glazing cavity (i.e. across the outside surfaces of the spaced glass).

Therefore, while the existing methods of determining gas concentration in insulating glass units can be used for laboratory research and testing of non-glazed sealed units, these methods cannot be employed effectively for routine quality control and field-testing purposes.

Furthermore, the ability to access and measure the level of gas within the glass assembly would allow the installer to add more gas when required and therefore maintain the insulating benefits of the glass.

Prior art glass assemblies have been devised to try and address the aforenoted problems. For example, U.S. Pat. No. 5,299,399 which issued on Apr. 5, 1994 to the inventors Bruce A. Baier et al. and was assigned to Pella Corporation of Pella, Iowa. This patent relates to a dual glazing window that has a removable glazing panel, which includes a breather system that connects the air chamber between the glazing panels with the outside ambient air by routing an outwardly facing channel into the window rail.

U.S. Pat. No. 2,880,475 issued on Apr. 7, 1959, and relates to a double glazed window unit suitable for use in a window, in which the space between the glass panels is evacuated to provide good insulating qualities and to prevent the formation of condensation due to temperature differences between the inner and outer panels.

U.S. Pat. No. 2,125,372 was issued on Aug. 2, 1938 and relates to a fitting for a glass sheet having a perforation and comprises of a metal connection plug having a threaded passage, which fits into the perforation for sealing the glass sheet.

U.S. Pat. No. 1,336,211 was issued on Apr. 6, 1920 to Henry Duffy of Longmont, Colorado and relates to an exteriorly threaded plug having a central port and a lateral passage with a valve seated in the passage, and having a transverse port.

Thus a gas concentration meter used for measuring the concentration of a gas within a sealed insulating unit or glass assembly and method thereof is desirable. Furthermore a non-obtrusive means of providing access to the insulating cavity to measure and/or replenish a gas within the cavity would be beneficial.

SUMMARY OF THE INVENTION

An object of one aspect of the present invention is to provide a gas concentration meter and improved insulating glass assembly and a method thereof.

In accordance with one aspect of the present invention there is provided a system for measuring the concentration of a gas within a sealed insulating cavity having an access means for communicating with the sealed insulating cavity, a probing means for insertion through the access means to the gas and having the ability to sense the concentration of the gas, and a measuring means for measuring and displaying the concentration of the gas through the probing means.

Conveniently, the access means is further defined as an access port assembly having a connecting means through the glazing spacer block and a stopping means.

Preferably, the connecting means spacer block may be defined as a connecting tube being integrally molded to a spacer block for insertion between the glass panes of the insulating unit.

In accordance with another aspect of the present invention, the probing means may be further defined as a pair of flexible electrodes which may be separated by a predetermined distance to form a gap.

In accordance with still another aspect of the invention, the measuring means may be defined as a meter having electronic circuitry to excite, control, monitor the excitation level, relate the excitation level to gas concentration through calibration means, and indicate or display the concentration level.

Another object of the present invention is to provide an improved method for measuring the concentration of a gas in a gas filled sealed insulating glazing assembly comprising of at least two spaced glass panes wherein the method comprises the following steps:

a) inserting a probing means through an access means for communication with the cavity of the gas filled insulating unit;

b) or placement of permanent probing means into the glazing cavity through the edge seal of the insulating unit;

c) or placement of permanent probing means in a gas sampling device such as a syringe or any other sampling container;

d) sensing the concentration of the gas with the probing means; and relaying the concentration of the gas to a measuring means for measuring the concentration of the gas.

Advantages of the present invention are:

a) ability to measure actual gas concentration on site or at the plant, b) ability to pressure equalize the glazing cavity in order to eliminate glass distortion or breakage, and c) ability to re-fill the insulated units with gas if gas-filling was deemed inadequate, thereby reducing the number of gas-filled units that have to be replaced.

BRIEF DESCRIPTION OF THE DRAWINGS

A detailed description of the preferred embodiment is provided herein below by way of example only and with reference to the following drawings, in which.

Figure 1:
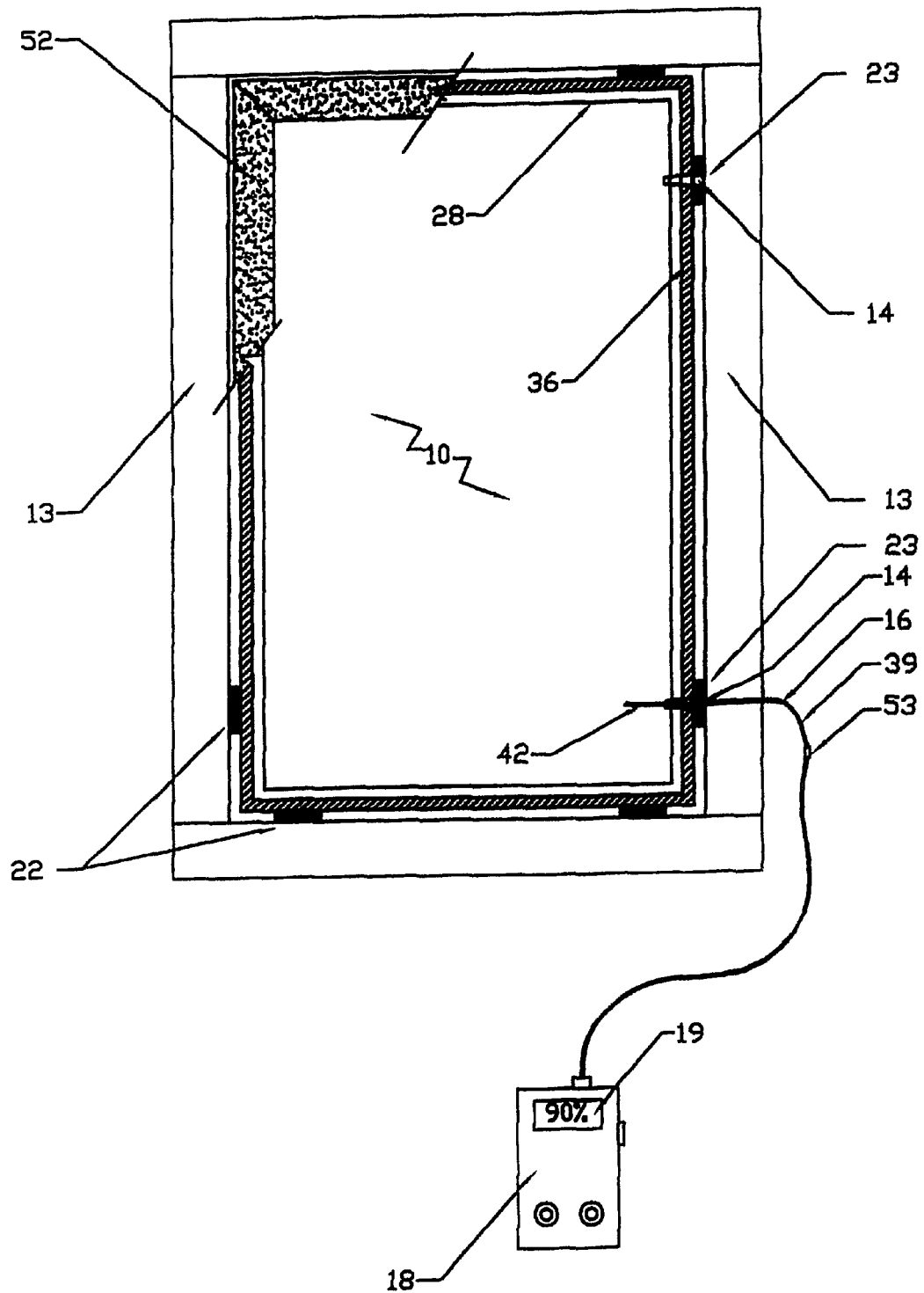
FIG. 1 in a side cross-sectional view, illustrates a conventional insulating glass assembly with the meter.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 2:
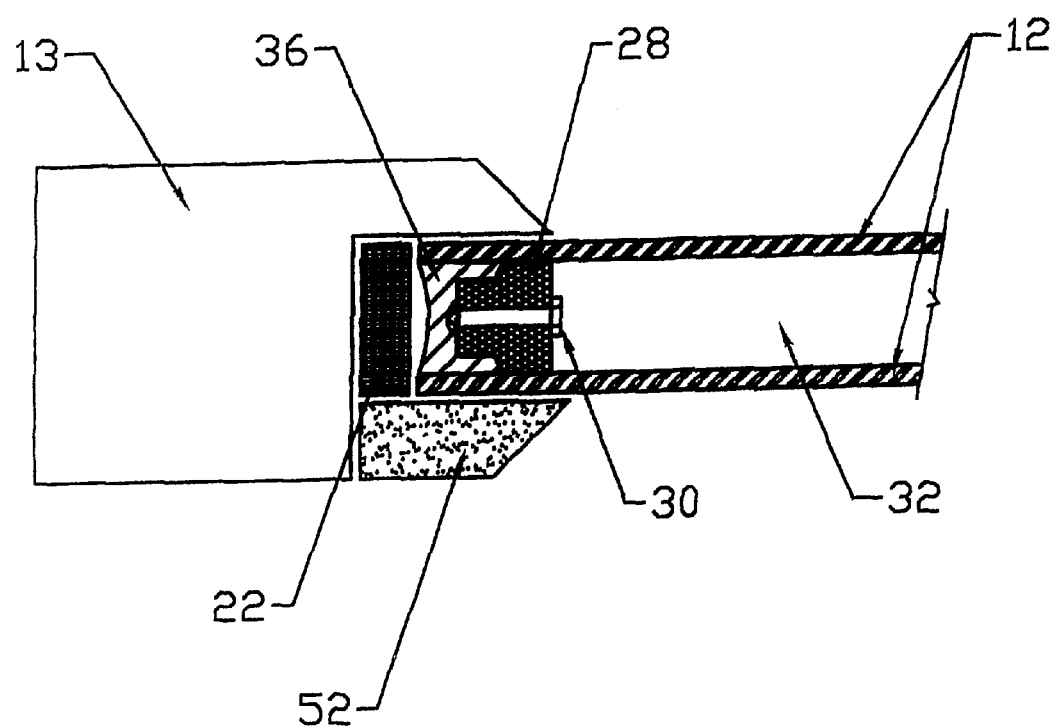
FIG. 2 in a side cross-sectional view, illustrates the insulating glass assembly in accordance with the preferred embodiment of the present invention.

Referring to FIGS. 1 and 2, there is illustrated in a cross-sectional side view, a system for measuring the concentration of a gas within a sealed insulating cavity 10 comprising of a sealed insulating glass units 11, defined by two glass panes 12 separated by edge spacer 28 and edge seal 36, in accordance with the preferred embodiment of the present invention.

The system 10 includes an access means 14 for communicating with the sealed cavity 32 of the sealed insulating glass units 11, a probing means 16 for insertion through the access means 14 to the gas filled sealed cavity 32 and for sensing the concentration of the gas, and a measuring means 18 for measuring and displaying the concentration of the gas that is sensed through the probing means 16.

The access means 14 may be further defined as an access port assembly 20, whereby the access port assembly 20 can comprise of a connecting means spacer block 23 and a stopping means 24. The connecting means spacer block 23 may include a connecting tube 26 that may be integrally molded to a conventional spacer block 22. The connecting tube 26, permanently inserted and sealed in passage 30 made through the edge seal 36 and edge spacer 28, connects the cavity 32 between the glass panes 12 to the outside environment. More particularly the passage 30 may be a 90-degree bore 34 made through the spacer block 23 which terminates at the connecting tube 26.

The stopping means 24 may be further defined as a resealable knock-out cap 37 which allows for temporary access to the cavity 32 via the passage 30 and the connecting tube 26. The spacer block 23 with connecting tube 26 may be made from a variety of materials and may be employed in any number positioned at any location around the perimeter of the sealed insulating glass unit 11 being used.

Alternatively, system 10 includes a probing means 16 permanently incorporated into the gas filled insulating glass unit 11 by means of insertion through the edge seal 36 for sampling and sensing the concentration of the gas, and a measuring means 18 for measuring and displaying the concentration of the gas that is sensed through the probing means 16.

The probing means 16 may be further defined as a pair of flexible electrodes 38. The flexible electrodes 38 (by way of example 26 Gage fine electrical wires) may be separated from one another by a pre-determined distance to form a gap 40. More specifically the flexible electrodes 38 may be in the form of a ribbon having exposed tips 42 or sensing means at one end that may be placed within the cavity 32, while the other end of the flexible electrodes 38 are connected to the measuring means 18 by means of electrical connector 53.

The flexible electrodes 38 may be made from a variety of materials and may have different distances for the gap 40 as the capacities, calibration and environment for the flexible electrodes 38 can vary. The location and connection of the flexible electrodes 38 can also vary. More specifically, the flexible electrodes 38 may be integrated with the spacer block 23 so that the sensing means 42 of the flexible electrodes 42 extend from the connecting tube 26 of the spacer block 23 and the exposed end 39 of the flexible electrodes 38 can be connected into the measuring means 18.

The sealed insulating glass units 11 may be contained within a frame 13, such as a window or doorframe, and secured within the frame 13 by a removable glazing stop 52. For measuring gas concentration in glazing cavity 32 or gas replenishing should the gas concentration within the insulating unit get too low, the glazing stop 52 may be removed to reveal the stopping means 24 located at the edge of the spacer block 23. The glazing cavity 32 may be accessed by removing the stopping means 24. Following gas concentration measurement or gas replenishment, the stopping means 24 can then be placed back and resealed. Alternatively, if a permanent probing means 16 is employed, the glazing stop 52 may be removed to reveal the exposed end 39 of the flexible electrodes 38 which can be connected into the measuring means 18 for sampling and measuring the gas concentration.

The measuring means 18 may be further defined as a meter 44 having electronic circuitry 46. The meter 44 excites the sensing end 42 of the probing means 16, controls, monitors the excitation level, relates the excitation level to gas concentration through calibration means, and indicates or displays the gas concentration level. Through the electronic circuitry 46, and more specifically a circuit board 50, an excitation signal is applied to the flexible electrodes 38 so as to create an arc therebetween at the sensing means 42. The meter 44 may be developed into a hand-held instrument, battery operated or an electronic stationary device. In general, meter 44 could be operated by a battery requiring one or more 1.5.V AA size batteries. The concentration of the gas may be calculated through calibration and scaling circuit, and displayed on the meter 44 through a LCD/LED display 19 or through a variety of other visual display methods such as digital, graphic, analogue or interfaced with a computer for logging or process control. The concentration of the gas may also be indicated visually by a colour change of chemically sensitized medium or identifier or through a sound effect such as a buzzer.

The meter 44 may be calibrated to read a variety of gases such as Argon, Krypton or any mixture of inert gases. Calibration of the meter 44 is conducted using the type of gas to be tested and either standard hardware or software such as an embedded programmed chip.

In operation, the method for measuring the concentration of a gas the probing means 16 creates an arc within the sealed insulating cavity 32 having electrical breakdown voltage proportionate to the concentration of the gas as governed by Paschen's law described below.

Pachen's law essentially states that the breakdown voltage characteristics of a gap are a function (generally not linear) of the product of the gas pressure and the gap length, usually written as V =f (p d) where "p" is the pressure and "d" is the gap distance. In actuality, the gas density should replace the pressure.

Pachen's law states that the breakdown voltage will remain constant as long as the gas density and gap length remain constant. By way of example, the breakdown voltage is a constant where the gap length is halved and the gas density is doubled. Therefore the breakdown voltage will be dependent on the gas density and on the type, shape and spacing of the flexible electrodes 38 at the sensing means 42. Knowing the breakdown voltage of the arc developed across the electrodes 38 at the sensing end means 42 having known electrode properties, the gas concentration is thus determined.

Figure 3:
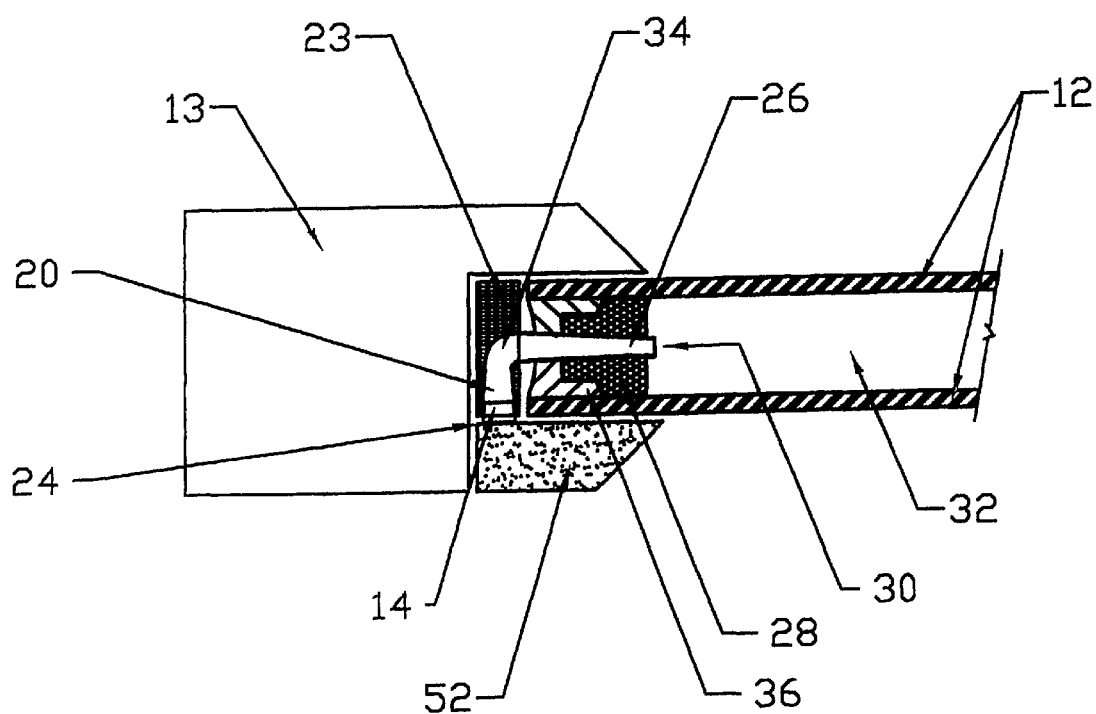
FIG. 3 in a perspective view, illustrates the system in accordance with the preferred embodiment of the present invention.
Figure 4:
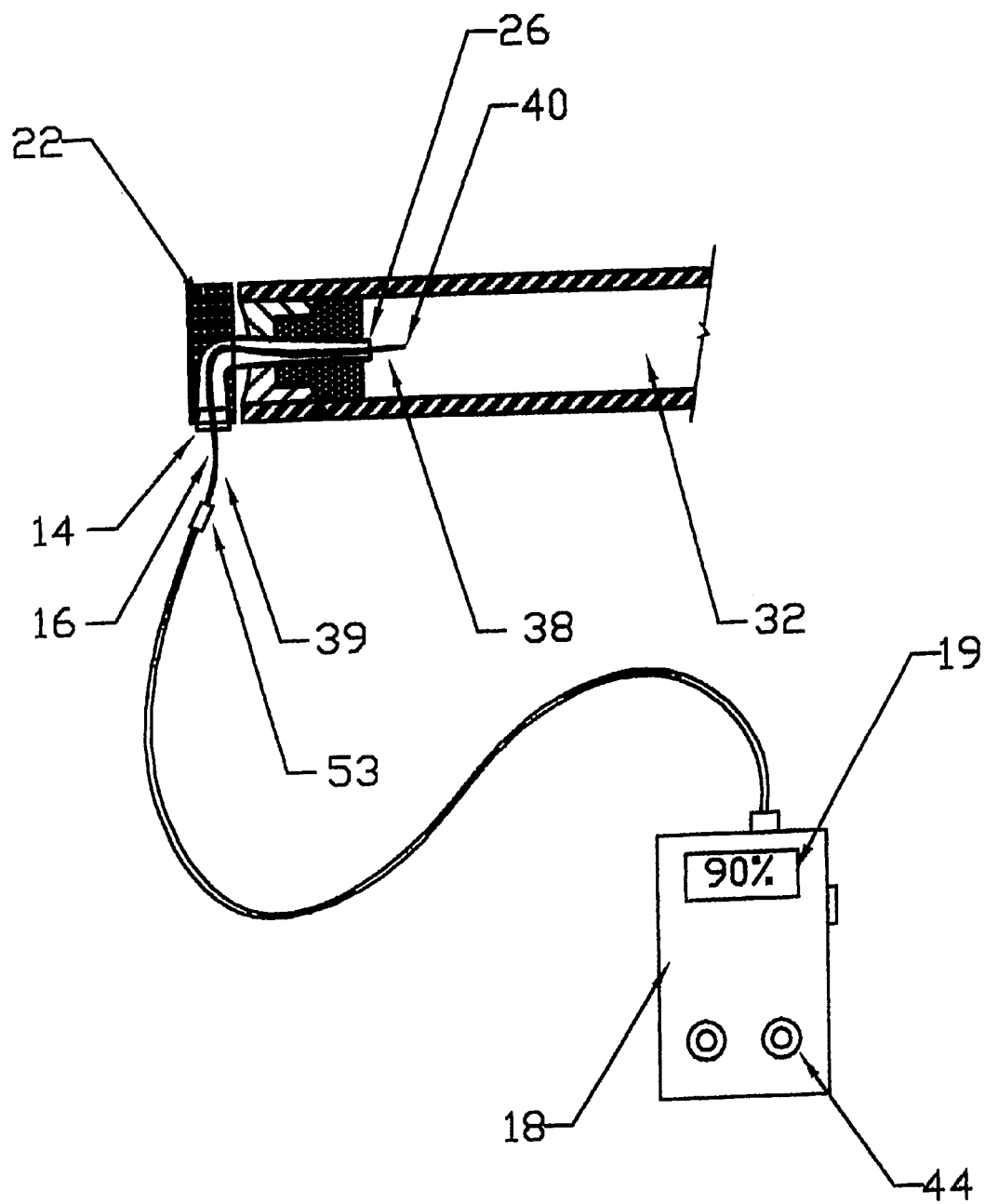
FIG. 4 in a top plan view, illustrates the meter in accordance with the preferred embodiment of the present invention.
Figure 5:
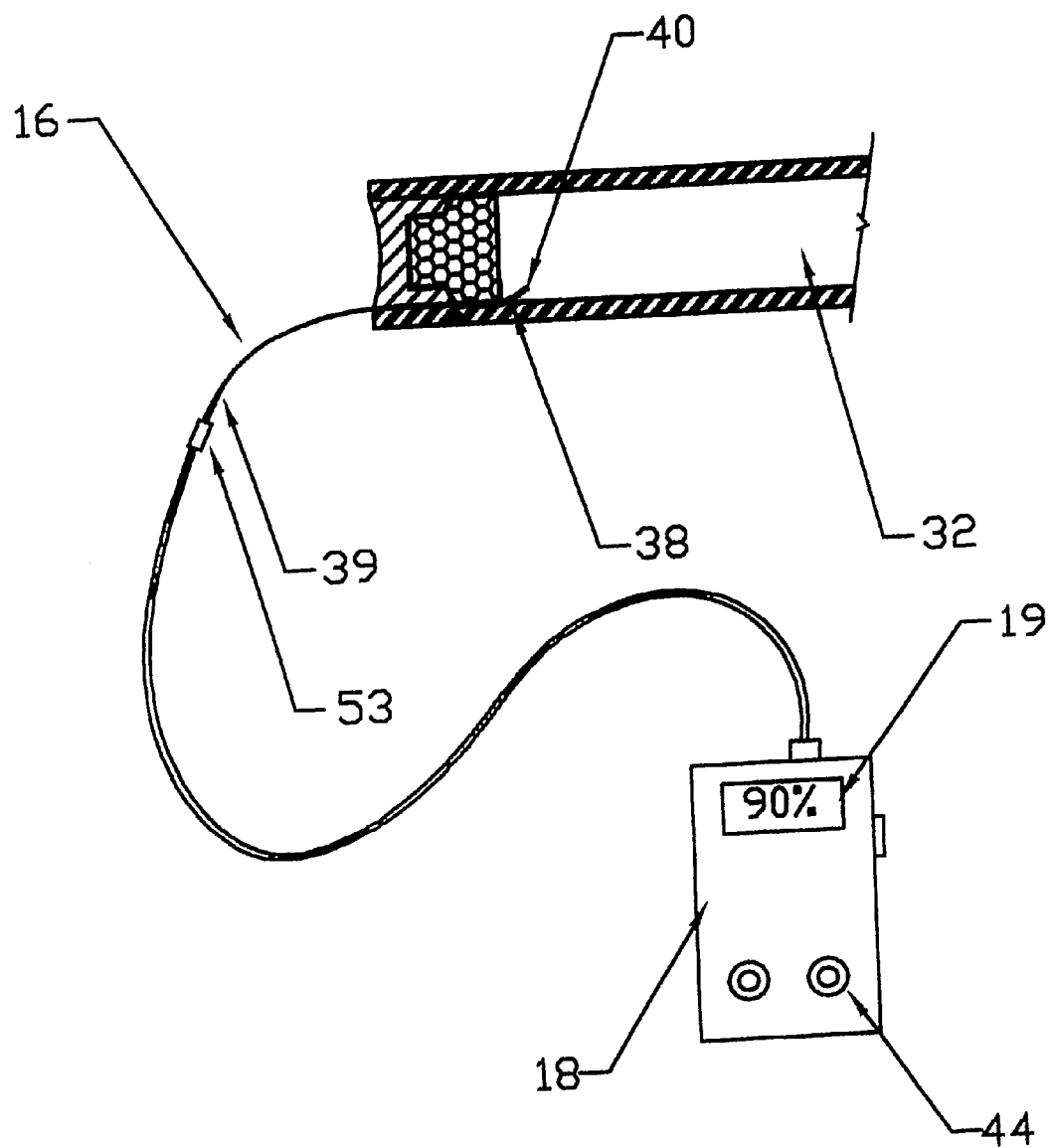
FIG. 5 in a cross-sectional view, illustrates the probing means being inserted into the access means in accordance with the preferred embodiment of the present invention.
Figure 6:
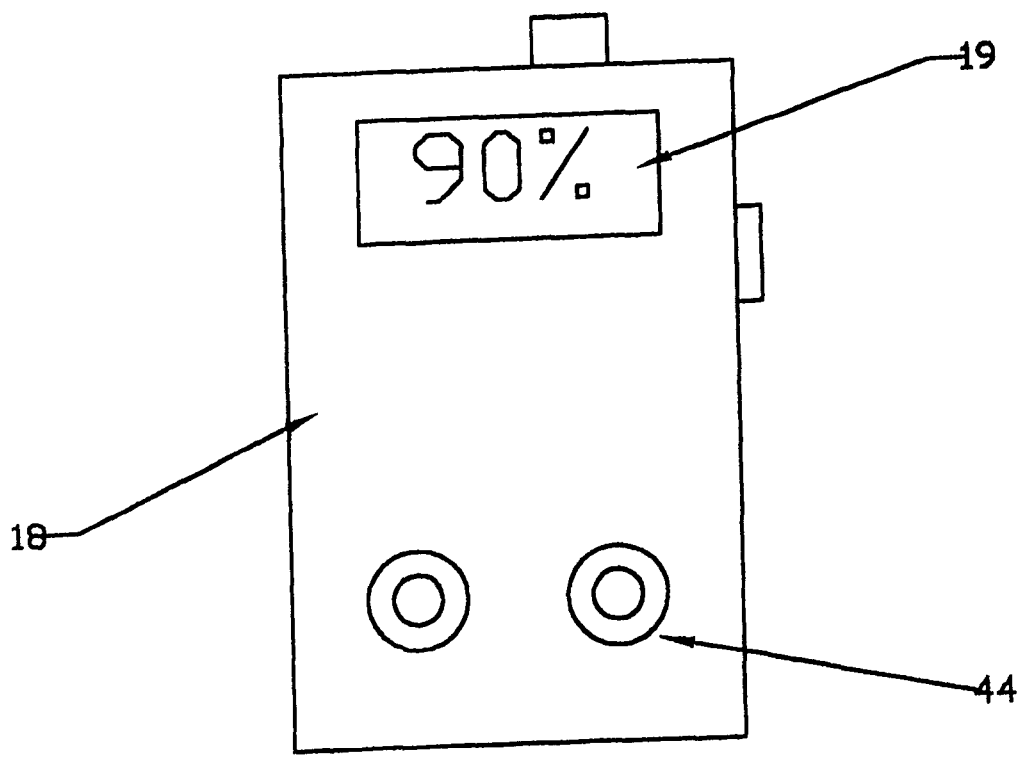
FIG. 6 in a cross-sectional view, illustrates the probing means being permanently installed into the glazing cavity in accordance with the preferred embodiment of the present invention.
Figure 7:
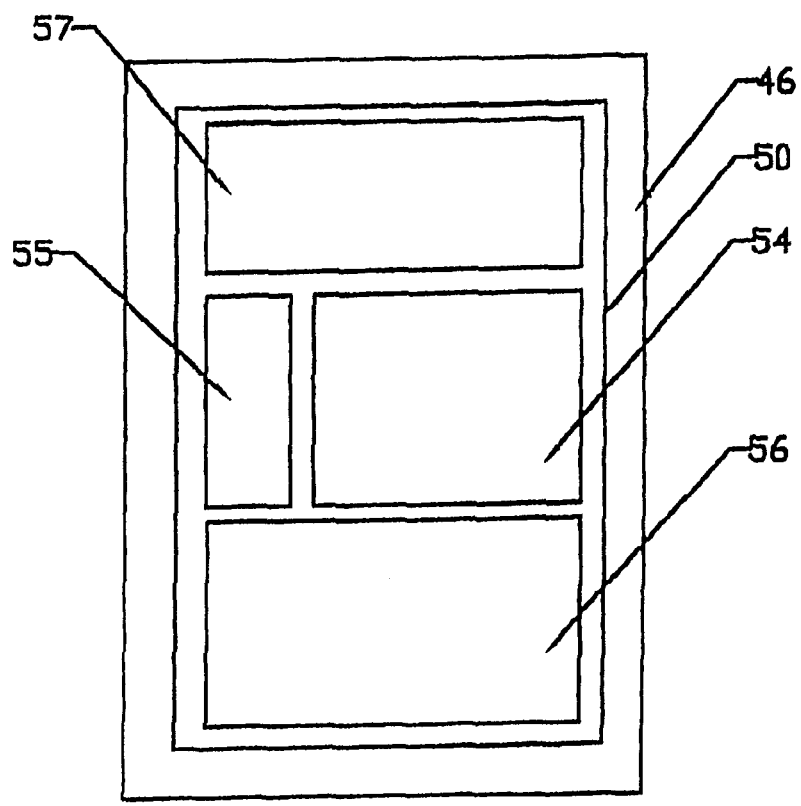
FIG. 7 in a top plan view, illustrates the circuitry in accordance with the preferred embodiment of the present invention.

Referring to FIG. 3, the user would temporarily remove the glazing stop 52 to reveal the stopping means or knockout cap 24 located at the side of the spacer block 23. The stopping means 24 may be removed and the probing means 16 or flexible electrodes 38 may then be inserted into the passage 30. As the flexible electrodes 38 are flexible, they will bend around the 90-degree bore 34 through the spacer block 23 and the connecting tube 26 to the cavity 32 located between the glass panes 12. Alternatively, in permanent electrode installation, the electrodes 38 extend outside of the edge spacer 28 of the sealed unit as previously described.

Upon placing the flexible electrodes 38 within the cavity 32, the sensing end 42 is excited, so that arcing occurs across the gap 40 between the exposed tips 42 of the flexible electrodes 38 through the gas. The electronic circuitry 46 and more specifically the circuit board 50 controls the excitation level through circuit 54, and measures the breakdown voltage and the current through the electrodes 38 across the electrode gap 40 at the sensing end 42.

Once the breakdown voltage is stabilized through means of circuit 55, the gas concentration can then be sampled and calculated by calibration circuit 56 from the breakdown voltage relayed to the meter 44 by the flexible electrodes 38 and other parameters as governed by Paschen's law and derived through laboratory calibration. The results may be displayed on the meter through circuit 57 and a variety of display modes outlined above and in a variety of measurements such as percentage, parts per million etc.

The accuracy of the method and measurements may be improved by repeating the excitation of the sensing means 42 of the electrodes 38 several times and averaging all of the measured individual breakdown voltage values. Averaging of the results may be done automatically by programming the circuit's controller chip.

Other variations and modifications of the invention are possible. All such modifications or variations are believed to be within the sphere and scope of the invention as defined by the claims appended hereto.

I claim:

1. A metering system for measuring the concentration of a gas within a sealed insulating glass window having two spaced glass panes separated by an edge spacer, an edge seal and a cavity, from the outside of said window comprising:

(a) an access port assembly having a connecting tube having one end within said cavity and a second end outside, a spacer block and a stopping means, wherein said spacer block is mounted adjacent said edge seal and said connecting tube is mounted through said spacer block, said edge seal and said edge spacer, thereby connecting said cavity to the outside; said stopping means securing said second end of said connecting tube;

(b) a probing means for insertion through said access port assembly to said cavity for sensing said gas concentration; and (c) a measuring means for measuring, calibrating, scaling and displaying said gas concentration sensed by said probing means;

wherein said access port assembly allows access into said cavity by said probing means from the outside, said measuring means attached to said probing means allowing for the measurement of said gas concentration.

2. A metering system as claimed in claim 1 wherein said connecting tube is at a 90° angle integrally molded to said spacer block and said stopping means is a reusable knock-out cap.

3. A metering system as claimed in claim 1 wherein said probing means is a pair of flexible electrodes separated from one another by a predetermined distance, said predetermined distance dependent on said gas being measured.

4. A metering system as claimed in claim 3 wherein said pair of flexible electrodes is a ribbon having exposed tips at a first end and connected to said measuring means at a second end by an electrical connector.

5. A metering system as claimed in claim 4 wherein said probing means may be either permanently installed into said sealed insulating glass window or removable from said connecting tube.

6. A metering system as claimed in claim 4 wherein said measuring means is a meter having electronic circuitry to excite, control and monitor the excitation level of said flexible electrodes.

7. A metering system as claimed in claim 6 wherein said meter is hand-held and battery operated.

8. A metering system as claimed in claim 6 wherein said gas being measured is Argon, Krypton or any combination of inert gas.

9. A method of measuring the concentration of a gas within a sealed insulating glass window having two spaced glass panes separated by an edge spacer, an edge seal and cavity, from the outside of said window using a metering system comprising:

(a) inserting a pair of flexible electrodes separated from one another by a predetermined distance, said distance dependent on said gas being measured though an access port assembly having a connecting tube having one end within said cavity and a second end outside, a spacer block and a stopping means wherein said spacer block is mounted adjacent said edge seal and said connecting tube is mounted through said spacer block said edge spacer and edge seal for access by said probing means to said cavity and said gas; thereby connecting said cavity to the outside; said stopping means securing said second end of said connecting tube;

(b) sampling and sensing said concentration of said gas by said flexible electrodes; and (c) relaying said concentration of said gas to a measuring means for measuring calibrating, scaling and displaying said gas concentration sensed by said flexible electrodes.

10. A method of measuring the concentration of a gas as claimed in claim 9 further comprising charging said flexible electrodes to a level at which the breakdown voltage produces arcing across said predetermined distance through said gas.

* * * * *